United States Patent [19]
Yoon

[11] Patent Number: 5,643,295
[45] Date of Patent: Jul. 1, 1997

[54] METHODS AND APPARATUS FOR SUTURING TISSUE

[76] Inventor: InBae Yoon, 2101 Highland Ridge Dr., Phoenix, Md. 21131

[21] Appl. No.: 377,723

[22] Filed: Jan. 25, 1995

Related U.S. Application Data

[63] Continuation-in-part of Ser. No. 366,285, Dec. 29, 1994.

[51] Int. Cl.$^6$ ............................................. A61B 17/04
[52] U.S. Cl. ................................. 606/151; 606/232
[58] Field of Search .................... 606/232, 233, 606/222, 224, 225, 226, 228, 148, 151; 112/156

[56]            References Cited

U.S. PATENT DOCUMENTS

| | | |
|---|---|---|
| 65,499 | 6/1867 | Miller ................................. 606/232 |
| 279,693 | 6/1883 | Blinn ................................. 606/224 |
| 722,105 | 3/1903 | Hervey ............................... 606/222 |
| 1,321,011 | 11/1919 | Cottes ............................... 606/223 |
| 1,852,098 | 4/1932 | Anderson . |
| 2,075,508 | 3/1937 | Davidson . |
| 2,199,025 | 4/1940 | Conn . |
| 3,033,204 | 5/1962 | Wood . |
| 3,541,591 | 11/1970 | Hoegerman . |
| 3,570,497 | 3/1971 | Lemole . |
| 3,580,256 | 5/1971 | Wilkinson . |
| 3,625,220 | 12/1971 | Engelsher . |
| 3,664,345 | 5/1972 | Dabbs et al. . |
| 3,753,438 | 8/1973 | Wood et al. ....................... 606/232 |
| 3,775,825 | 12/1973 | Wood et al. . |
| 3,802,438 | 4/1974 | Wolvek . |
| 3,831,608 | 8/1974 | Kletschka et al. . |
| 3,857,396 | 12/1974 | Hardwick . |
| 3,910,281 | 10/1975 | Kletschka et al. ................ 606/232 |
| 3,931,821 | 1/1976 | Kletschka et al. . |
| 3,976,079 | 8/1976 | Samuels et al. ................... 606/233 |
| 4,006,747 | 2/1977 | Kronenthal et al. . |
| 4,069,825 | 1/1978 | Akiyama . |
| 4,235,238 | 11/1980 | Ogiu et al. ........................ 606/145 |
| 4,291,698 | 9/1981 | Fuchs et al. . |
| 4,387,489 | 8/1983 | Dudek . |
| 4,440,171 | 4/1984 | Nomoto et al. . |
| 4,669,473 | 8/1987 | Richards et al. . |
| 4,750,492 | 8/1988 | Jacobs . |
| 4,932,962 | 8/1990 | Yoon et al. . |
| 4,935,027 | 8/1990 | Yoon . |
| 4,950,285 | 8/1990 | Wilk . |
| 4,969,892 | 11/1990 | Burton et al. . |
| 4,982,149 | 1/1991 | Yoon et al. . |
| 5,009,663 | 4/1991 | Broome . |
| 5,037,433 | 8/1991 | Wilk et al. . |
| 5,053,047 | 10/1991 | Yoon . |
| 5,074,874 | 12/1991 | Yoon et al. ........................ 606/224 |
| 5,078,731 | 1/1992 | Hayhurst . |
| 5,100,418 | 3/1992 | Yoon et al. . |
| 5,123,913 | 6/1992 | Wilk et al. . |
| 5,129,912 | 7/1992 | Noda et al. . |
| 5,152,769 | 10/1992 | Baber . |
| 5,160,339 | 11/1992 | Chen et al. . |
| 5,171,251 | 12/1992 | Bregen et al. .................... 606/151 |
| 5,207,693 | 5/1993 | Phillips . |
| 5,207,694 | 5/1993 | Broome . |

(List continued on next page.)

FOREIGN PATENT DOCUMENTS

| | | | |
|---|---|---|---|
| 91/07916 | 6/1991 | WIPO ................................. 606/232 |
| 94/15535 | 7/1994 | WIPO ................................. 606/232 |

OTHER PUBLICATIONS

"Berry & Kohn's introduction to Operating Room Technique", Lucy Jo Atkinson and Mary Louise Kohn.

*Primary Examiner*—Michael Buiz
*Assistant Examiner*—Patrick W. Rasche

[57]            ABSTRACT

Apparatus and methods for suturing and ligating anatomical tissue utilizes one or more knotting elements connected between two or more length portions of filamentous suture material to form one or more contractible loops for confining segments of the length portions therein. The knotting elements receive the suture material to effect a knot for one or more adjustably tensioned stitches created when the segments are passed through the loop and the suture material is received by the knotting elements.

20 Claims, 6 Drawing Sheets

U.S. PATENT DOCUMENTS

| | | |
|---|---|---|
| 5,211,650 | 5/1993 | Noda . |
| 5,222,976 | 6/1993 | Yoon . |
| 5,234,449 | 8/1993 | Bruker et al. . |
| 5,259,846 | 11/1993 | Granger et al. .......................... 606/224 |
| 5,269,809 | 12/1993 | Hayhurst et al. . |
| 5,282,809 | 2/1994 | Kammerer et al. . |
| 5,282,832 | 2/1994 | Toso et al. . |
| 5,312,436 | 5/1994 | Coffey et al. . |
| 5,318,578 | 6/1994 | Hasson . |
| 5,320,629 | 6/1994 | Noda et al. . |
| 5,330,442 | 7/1994 | Green et al. . |
| 5,330,491 | 7/1994 | Walker et al. . |
| 5,330,503 | 7/1994 | Yoon . |
| 5,336,231 | 8/1994 | Adair . |
| 5,354,298 | 10/1994 | Lee et al. . |
| 5,366,459 | 11/1994 | Yoon . |
| 5,368,595 | 11/1994 | Lewis . |
| 5,370,661 | 12/1994 | Branch . |
| 5,376,101 | 12/1994 | Green et al. . |
| 5,383,905 | 1/1995 | Golds et al. . |
| 5,391,173 | 2/1995 | Wilk . |
| 5,411,522 | 5/1995 | Trott ........................................ 606/232 |

METHODS AND APPARATUS FOR SUTURING TISSUE

CROSS-REFERENCE TO RELATED PATENT APPLICATION

This application is a continuation-in-part of applicant's prior patent application Ser. No. 08/366,285 filed Dec. 29, 1994 and entitled Methods and Apparatus for Suturing Tissue, the disclosure of which is incorporated herein by reference.

BACKGROUND OF THE INVENTION

1. Field of the Invention

The present invention pertains to suturing of bodily tissue and, more particularly, to methods and apparatus for suturing tissue during endoscopic and open surgical procedures.

2. Discussion of the Prior Art

Suturing of bodily tissue is a time consuming part of most surgical procedures including both open surgery and endoscopic or minimally invasive surgery. By open surgery is meant surgery wherein the surgeon gains access to the surgical site via a relatively large incision, and by endoscopic surgery is meant surgery wherein the surgeon gains access to the surgical site via one or more portals through which endoscopes are introduced to view the surgical site and through which various instruments are introduced to the surgical site. There are many common endoscopic surgical procedures, including arthroscopy, laparoscopy (pelviscopy), gastroentroscopy and laryngobronchoscopy, for example. In the past, suturing has been accomplished with the use of a sharp metal suture needle attached to the end of a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed; however, knotting of the suture material is time consuming and tedious work, particularly in microsurgery and endoscopic surgery. In microsurgery, suturing is necessarily time consuming due to the limited space at the suture site, the small size of the suture needle and the suture material and the concomitant difficult manipulation required to pass the suture needle through the tissue and to tie a knot in the suture material. With respect to endoscopic surgery, suturing and tying knots represents an even more time consuming procedure due to the difficult maneuvers required. Accordingly, while endoscopic surgery would be preferred for most procedures, the advantages can be outweighed by the disadvantages caused by the length of time required to complete the endoscopic surgical procedure, which time is greatly extended due to the time required for suturing. It is extremely important for knotting or tying of sutures to be consistently performed to provide a stitch with controlled, non-slipping, tension; and, to this end, it is common for surgeons to tie double knots, that is, a first knot to control tension and a second knot to secure the first knot. Accordingly, it will be appreciated that there is a great need for improving the tying procedure involved in suturing to permit expedited knotting while also providing consistent, secure knots.

There have been many attempts to provide devices to take the place of conventional suturing with a suture needle and a length of suture material; however, such devices have essentially been staples, clips or clamps not facilitating adjustment of tension by the surgeon. French Patent No. 2,651,113 to Alain and U.S. Pat. No. 3,123,077 to Alcamo, U.S. Pat. No. 3,570,497 to Lemole, U.S. Pat. No. 4,548,202 to Duncan, U.S. Pat. No. 4,592,355 to Antebi, U.S. Pat. No. 4,730,615 to Sutherland et al, U.S. Pat. No. 4,935,028 to Drews, U.S. Pat. No. 4,950,285 to Wilk, U.S. Pat. No. 4,955,913 to Robinson and U.S. Pat. No. 5,123,913 to Wilk are representative of devices for use during open surgery to adjustably hold tissue together similar to suturing and tying but fail to provide the same feel and tension control as tying or knotting a length of suture material. U.S. Pat. No. 3,910,281 to Kletschka et al is representative of suture anchors for facilitating tying. U.S. Pat. No. 2,075,508 to Davidson, U.S. Pat. No. 2,199,025 to Conn and U.S. Pat. No. 3,664,345 to Dabbs et al are illustrative of suture buttons for retaining sutures. U.S. Pat. No. 3,976,079 to Samuels et al and U.S. Pat. No. 4,291,698 to Fuchs, deceased, et al, are representative of suture buttons having structure for clamping suture material. U.S. Pat. No. 4,750,492 to Jacobs discloses apparatus and method for suturing utilizing both an anchor and a clenching device.

Endoscopic surgery is preferred over open surgery due to the greatly reduced trauma and wound healing time for the patient and due to concomitant cost savings associated with shorter hospital stays and performing surgery in non-hospital or out-patient surgery sites. Accordingly, there has been much effort spent to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in endoscopic surgery to permit surgeons to suture with controlled tension and approximation of tissue similar to that obtained by conventional knot tying.

U.S. Pat. No. 3,541,591 to Hoegerman, U.S. Pat. No. 3,753,438 to Wood et al, and U.S. Pat. No. 3,775,825 to Wood et al disclose apparatus and methods for suturing wherein clips are secured on the free ends of a suture filament. U.S. Pat. No. 5,078,731 to Hayhurst, U.S. Pat. No. 5,160,339 to Chen et al, U.S. Pat. No. 5,171,251 to Bregen et al, U.S. Pat. No. 5,234,449 to Bruker et al, U.S. Pat. No. 5,181,832 to Toso et al and U.S. Pat. No. 5,330,442 to Green et al are representative of clips for clamping suture material to eliminate knotting during endoscopic procedures. European Patent Publication No. 0.477,020A to Chen et al and U.S. Pat. No. 5,015,250 to Foster, U.S. Pat. No. 5,037,433 to Wilk et al, U.S. Pat. No. 5,059,201 to Asnis, U.S. Pat. No. 5,084,058 to Li, U.S. Pat. No. 5,087,263 to Li, U.S. Pat. No. 5,100,415 to Hayhurst, U.S. Pat. No. 5,100,421 to Christoudias, U.S. Pat. No. 5,144,961 to Chen, U.S. Pat. No. 5,147,373 to Ferzli, U.S. Pat. No. 5,152,769 to Baber and U.S. Pat. No. 5,163,946 to Li are representative of needle holders and apparatus for suturing, knotting or ligating during endoscopic procedures. The above techniques and instruments have the disadvantages of requiring complex instruments, of requiring special suture devices, of being difficult to manipulate and/or of not sufficiently reducing the time required for suturing and tying or knotting.

U.S. Pat. No. 4,932,962, U.S. Pat. No. 4,981,149, U.S. Pat. No. 5,074,874 and U.S. Pat. No. 5,100,418 to Yoon et al and U.S. Pat. No. 4,935,027, U.S. Pat. No. 5,053,047, U.S. Pat. No. 5,222,076, U.S. Pat. No. 5,330,503 and U.S. Pat.

No. 5,336,459 to Yoon disclose methods and apparatus particularly useful for suturing during endoscopic procedures to permit tissue approximation with controlled tension.

SUMMARY OF THE INVENTION

Accordingly, it is a primary object of the present invention to provide apparatus and methods for suturing anatomical or bodily tissue in a time efficient, consistent and precise manner.

Another object of the present invention is to utilize a single, plastically deformable knotting element to form a knot between opposite ends of a stitch of first and second length portions of filamentous suture material forming a contractible loop and, further, to use a plurality of such knotting elements with first and second length portions of filamentous suture material forming a plurality of contractible loops to form a plurality of stitches in tissue in an expeditious manner.

A further object of the present invention is to suture anatomical tissue utilizing a suturing apparatus including a needle, first and second length portions of filamentous suture material extending from the needle and at least one knotting element connected between first segments of the first and second length portions to form a loop with the suture material extending from the needle to the knotting element and back to the needle, each knotting element having a grasping site including opposed surfaces having a first position for receiving second segments of the first and second length portions and a second position to grasp the second segments to effect a knot to form a suture stitch in the anatomical tissue after the needle has been passed through the loop, the suture material has been tensioned to contract the loop and the second segments have been received between the opposed surfaces.

The present invention has another object in that a plurality of knotting elements are arranged in series along first and second length portions of suture material to form contractible loops between two knotting elements, each of the knotting elements including at least one site for engaging first segments of the first and second length portions and at least one site for engaging second segments of the first and second length portions.

An additional object of the present invention is to secure a plurality of knotting elements at spaced positions along first and second length portions of filamentous suture material to define contractible loop stitch segments between two knotting elements with the knotting elements acting as knots for the contractible loop stitch segments when the contractible loop stitch segments are passed through or around anatomical tissue and segments of the first and second length portions are passed through the contractible loops and back to the knotting elements.

It is also an object of the present invention to suture anatomical tissue utilizing a suture supply having at least one first length portion and at least one second length portion of filamentous suture material and at least one knotting element connected between segments of the first and second length portions to form a contractible loop with the knotting element having at least one grasping site for grasping other segments of the first and second length portions to tie a stitch formed when the other segments are passed through the loop and positioned between opposed surfaces of the knotting element.

The present invention has as an additional object to suture anatomical tissue by penetrating the tissue with a needle from an entry point to an exit point to pass first and second length portions of filamentous suture material through the tissue, passing segments of the first and second length portions exiting the tissue at the exit point through a contractible loop formed by the first and second length portions and a knotting element connecting other segments of the first and second length portions to form a stitch segment extending from the knotting element through the tissue and back to the knotting element, positioning the segments passed through the loop to be received by the knotting element and plastically deforming the knotting element to grasp the segments received therein.

It is a further object of the present invention to form a stitch in anatomical tissue by positioning first and second length portions of filamentous suture material connected by a knotting element around the tissue, passing segments of the first and second length portions through a loop formed by the first and second length portions and the knotting element to form a stitch extending from the knotting element around the tissue and back to the knotting element, contracting the loop and positioning the segments to be engaged by the knotting element.

Some of the advantages of the present invention are that segments of the first and second length portions are confined by the contractible loop for enhanced ease of suturing and greater control, positioning segments of the first and second length portions at the grasping site is facilitated by confinement of the suture material length portions by the loop, segments of the first and second length portions can be positioned at the grasping site concomitant with contracture of the loop the suture stitch formed thereby is of increased strength, a single suture supply can be used for suturing with penetration through the tissue or for ligation, controlled tissue approximation can be achieved to provide a "feel" similar to suturing with knot tying in an expeditious manner for use in open or endoscopic procedures, the variety of surgical procedures that can be performed endoscopically without increasing the time required for suturing is expanded, suturing can be accomplished using standard filamentous suture materials, suturing can be accomplished using standard, available instruments or specially designed instruments of simple construction allowing the instruments to be disposable or easily sterilizable for reuse, a plurality of stitches can be formed without having to withdraw instruments from the body after completion of each stitch as is particularly advantageous for endoscopic use, the size of the stitch segments can be selectively adjusted during use, enhanced securement of suture stitches is realized to ensure that completed stitches remain intact, the knotting elements can be optimally oriented to engage the suture material for certain procedures and the amount of space required for suturing is minimized These and other objects, advantages and benefits are realized with the present invention as generally characterized in a suturing apparatus including first and second length portions of filamentous suture material having ends received by a needle and a knotting element connected with first segments of the first and second length portions to form a loop with the suture material extending from the needle to the knotting element and back to the needle. The loop is contractible to confine therein second segments of the first and second length portions after the needle has been passed through the loop. The knotting element has a grasping site including a pair of opposed surfaces for grasping the second segments, the opposed surfaces being movable to non-releasably grasp the second segments to effect a knot after the needle has been passed through the loop and the suture material received between the opposed surfaces. The present invention is further generally characterized in a suture supply including first and second length portions of filamentous suture material and a plurality of knotting elements arranged in series along the first and second length portions and each connected between a first segment of the first length portion and a first segment of the second length portion to form a contractible loop between two knotting elements. Each knotting element has a grasping site for grasping a second segment of the first length portion and a second segment of the second length portion to act as a knot for stitch segments defined between the first and second segments. The present invention is additionally generally characterized in a suture supply including at least one first length portion and at least one second length portion of filamentous suture material and at least one knotting element connected between the first and second length portions to form at least one contractible loop, the knotting element having at least one attachment site at which segments of the first and second length portions are secured to the knotting element and at least one grasping site including opposed surfaces for grasping other segments of the first and second length portions to tie a stitch formed when the other segments are passed through the loop and positioned between the opposed surfaces of the knotting element. The present invention is also generally characterized in a method of suturing anatomical tissue comprising the steps of penetrating the tissue with a needle from an entry point to an exit point to pass first and second length portions of filamentous suture material through the tissue, passing segments of the first and second length portions exiting the tissue at the exit point through a contractible loop formed by the first and second length portions and a knotting element connecting other segments of the first and second length portions to form a stitch extending from the knotting element through the tissue and back to the knotting element, positioning the segments passed through the loop to be received by the knotting element, contracting the loop to tighten the stitch and plastically deforming the knotting element to grasp the segments received therein.

DESCRIPTION OF THE PREFERRED EMBODIMENTS

Figures 1, 2:
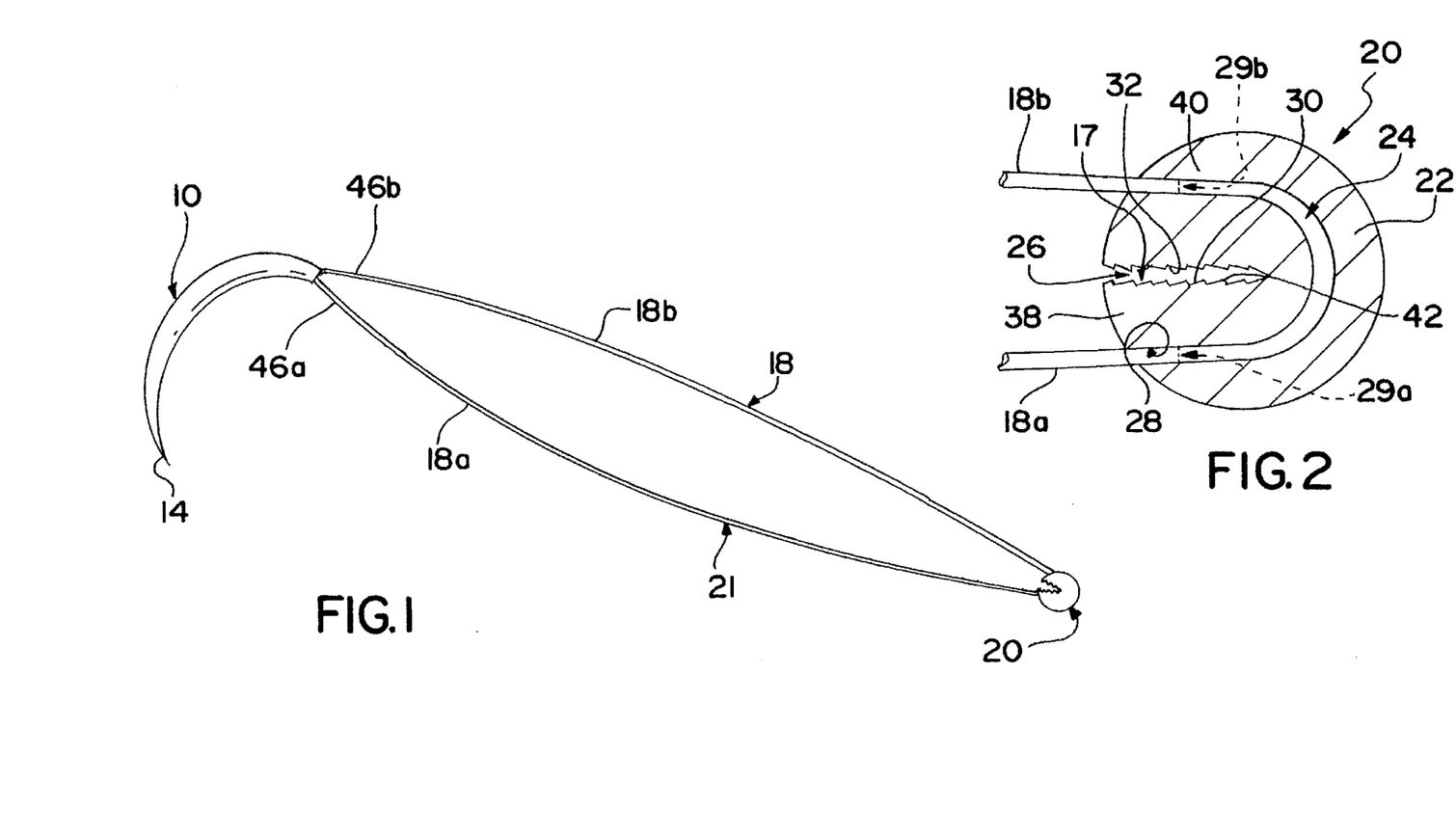
FIG. 1 is a perspective view of a suturing apparatus according to the present invention.
FIG. 2 is a broken side view, partly in section, of a knotting element for the suturing apparatus according to the present invention.

A suturing apparatus in accordance with the present invention is shown in FIG. 1 and includes first and second length portions 18a and 18b of filamentous suture material 18 extending between a needle 10 and a knotting element 20. Suture material length portions 18a and 18b can be defined by separate, discrete lengths of suture material having proximal ends coupled with knotting element 20 without passing entirely through the knotting element 20, which thusly serves to connect the length portions, and distal ends coupled with needle 10 or by a single length of suture material 18 passing through knotting element 20 and extending therefrom to terminate at distal ends 46a and 46b as shown in FIGS. 1 and 2. Ends 46a and 46b are secured to or attached or coupled with needle 10 having a sharp distal tip 14 for penetrating anatomical tissue, the ends 46a and 46b being secured to a proximal end of needle 10. Accordingly, the length of suture material 18 extends from the needle 10 through the knotting element 20 and back to the needle 10 to form a contractible loop or passage 21 defined by length portions 18a and 18b and knotting element 20.

The suture material can be made of non-stretchable or stretchable, absorbable or non-absorbable materials, and the suture material can have various outer diameter or cross-sectional sizes in accordance with procedural use including sizes suitable for use in microsurgical procedures. The suture material can be solid or hollow; and, where hollow, small holes can be formed in the wall of the suture material to communicate with the hollow interior thereof. Various substances, such as medicaments, can be supplied within the hollow interior of the suture material to leach out through the holes and enter tissue in which the suture material is placed. The suture material length portions 18a and 18b can have a length between needle 10 and knotting element 20 dependent upon the type of stitch to be performed.

Needle 10 can have various configurations such as curved as shown in FIG. 1, straight, circular, coiled or spiraled or the like and can be made of non-absorbable or absorbable materials. The suture material length portions 18a and 18b can be secured or attached to or coupled with needle 10 in many various ways including being secured in a blind hole in the needle, being fused, bonded, welded or molded with the needle or passing partly or entirely through the needle. The suture material length portions can be secured to or coupled with the needle anywhere along the body of the needle.

Knotting element 20 is best shown in FIG. 2 and has one or more attachment sites for receiving first segments of the suture material length portions 18a and 18b, respectively, prior to suturing and one or more grasping sites for engaging second segments of the suture material length portions 18a and 18b, respectively, after suturing to form a stitch. Knotting element 20 is formed of a substantially spherical body 22 of a medical grade, absorbable or non-absorbable, plastically deformable or malleable material, integrally and unitarily defining an attachment site 24 and a grasping site 26. The attachment site 24 includes a bore or passage 28 in body 22 with the suture material 18 passing through the bore 28 such that the knotting element is carried by the suture material with proximal ends or segments of the suture material length portions 18a and 18b, respectively, connected with the knotting element. Body 22 is formed to define legs, jaws or opposing portions 38 and 40 terminating at distal ends and carrying opposed surfaces 30 and 32, respectively, provided with gripping and/or locking structure such as teeth 42. The knotting element 20 is normally disposed in an open or suture material-receiving position wherein the distal ends of jaws 38 and 40, respectively, are spaced from one another to define an opening or mouth 17 therebetween, and the inner opposed surfaces 30 and 32 define a grasping site for engaging respective second segments of the suture material length portions 18a and 18b as explained further below. The knotting element can be provided with more than one grasping site, and the one or more grasping sites can be located anywhere along the knotting element.

As shown in FIG. 2, bore 28 follows a U-shaped path through knotting element 20 and has substantially straight bore segments joined by a curved bore segment; however, the bore 28 can follow various straight, angular and/or curved paths through the knotting element, and the one or more attachment sites can be located anywhere along the knotting element. The straight bore segments extend through the jaws 38 and 40 on opposite sides of mouth 17 such that mouth 17 opens into or faces loop 21 between suture material length portions 18a and 18b. Although loop 21 is shown in FIG. 1 in an open position defining an actual space between suture material length portions 18a and 18b, which are spaced from one another, it should be appreciated that suture material length portions 18a and 18b will be disposed adjacent one another during use when passed together through tissue and/or tensioned to form a stitch as described further below. Although bore 28 for knotting element 20 defines a single, unitary and integral attachment site for both suture material length portions 18a and 18b, it should be appreciated that separate and discrete attachment sites can be provided for the respective length portions, which are connected by the knotting element to form the contractible loop. For example, where the suture material length portions are formed by separate lengths of suture material, the separate lengths of suture material can have the proximal ends thereof attached to knotting element 20 at separate attachment sites such as being received in separate bores or holes 29a and 29b in the knotting element as shown in dotted lines in FIG. 2. The knotting element 20 can be slidable relative to the suture material or fixed along the suture material as disclosed in the prior application. Various knotting elements suitable for use in the present invention are disclosed in the prior application including knotting elements having tails formed by the suture material extending therefrom and various locking and/or gripping structure. The knotting element 20 can be moved to the closed position and plastically deformed as disclosed in the prior application with the use of conventional instruments including graspers, clamps, forceps or the like.

Figures 3, 4, 5, 6, 7, 8:
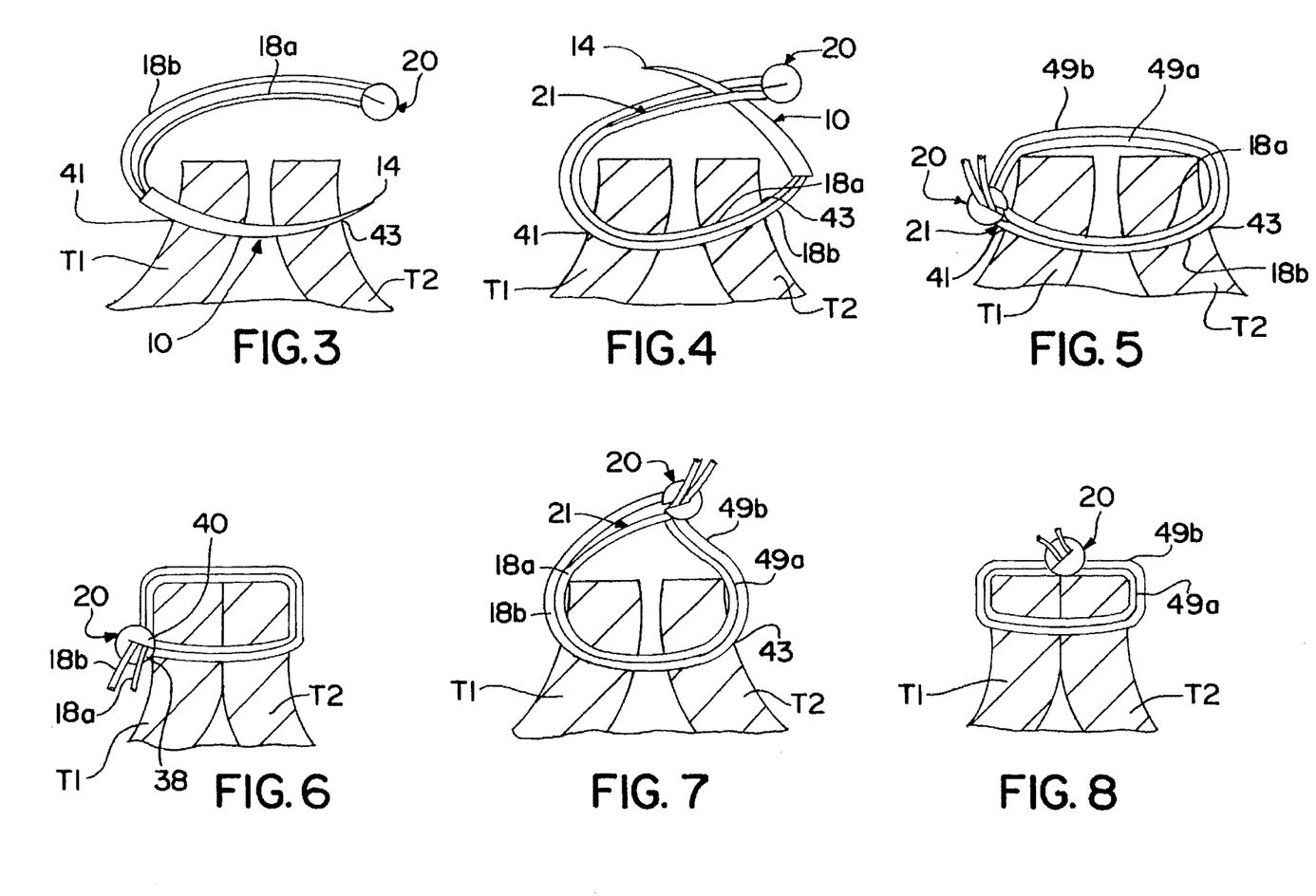
FIGS. 3, 4, 5 and 6 are broken side views, partly in section, illustrating use of the suturing apparatus according to the present invention.
FIGS. 7 and 8 are broken side views, partly in section, illustrating alternative use of the suturing apparatus according to the present invention.

FIGS. 3–6 illustrate use of the suturing apparatus of FIG. 1 during which the needle 10 can be manipulated by a needle holder or driver, and the knotting element 20 can be manipulated and/or moved to the closed position by a grasping instrument as disclosed in the prior application. To suture tissue portions T1 and T2, the needle 10 is driven, tip first, distally or forwardly through an entry point 41 in tissue portion T1 and then through tissue portion T2 and out of tissue portion T2 at an exit point 43 pulling the double filament defined by suture material length portions 18a and 18b through the tissue portions as shown in FIGS. 3 and 4. Once needle 10 has passed through tissue portion T2, the needle is passed through the contractible loop 21 as shown in FIG. 4, and the length portions are pulled to contract, tighten or close loop 21 until the knotting element 20 contacts tissue portion T1 at the entry point 41. Accordingly, segments 49a and 49b of suture material length portions 18a and 18b, respectively, extending from the exit point 43 will be drawn back over the tissue portions T1 and T2 to the entry point 41 and will be confined, held, clamped or gripped by the thusly tightened loop 21. The segments 49a and 49b passing through loop 21 are positioned to be engaged by the knotting element 20 to be received between jaws 38 and 40 such that a stitch is formed extending from the knotting element through the tissue and back to the knotting element with the knotting element effecting or serving as a knot for the suture stitch. By pulling the suture material to contract, tighten or close loop 21, the suture material segments 49a and 49b can be caused to enter the mouth 17 due to confinement of the suture material by the loop to thusly facilitate positioning of the suture material to be received by the knotting element. Once the knotting element 20 has been drawn up against the tissue and segments 49a and 49b have been brought back over the tissue and passed through loop 21 to be received by the knotting element, tension is applied to the suture material to tighten the suture stitch to adjustably approximate tissue portions T1 and T2 as shown in FIG. 6. Thereafter, knotting element 20 is plastically deformed to the closed position utilizing the grasping instrument to squeeze jaws 38 and 40 to clamp the jaws together to grip the suture material segments and secure the thusly formed tensioned suture to complete the stitch. The suture material length portions are then cut to remove any excess material, and the excess suture material and the needle are removed from the body. Although the suturing procedure has been described for two tissue portions T1 and T2, it should be appreciated that the procedure is applicable to suturing of various tissue structures including single and multiple tissue structures, puncture sites and wound closures and ligation, for example. With the use of length portions 18a and 18b, suturing is enhanced in that segments of the suture material length portions are confined by the contractible loop and clamped thereby after the loop is tightened. Additionally, the segments can be positioned to be received at the grasping site in response to or simultaneous with contracture of the loop to simplify and reduce the steps required for suturing.

FIGS. 7 and 8 illustrate alternative use of the suturing apparatus of FIG. 1 wherein the segments 49a and 49b are passed through the loop 21, and the suture material length portions 18a and 18b are pulled in a direction to contract loop 21 and cause the segments 49a and 49b to enter the mouth 17 and form a stitch extending from the knotting element through the tissue portions T1 and T2 and back to the knotting element, which is positioned between the tissue portions. Continued pulling of length portions 18a and 18b causes the stitch to be adjustably tensioned or tightened to approximate tissue portions T1 and T2 with the knotting element 20 disposed along the interface of tissue portions T1 and T2 as shown in FIG. 8. The knotting element is then moved to the closed position and plastically deformed causing jaws 38 and 40 to grip the suture material segments therebetween and secure the thusly formed tensioned suture to complete the stitch.

It should be appreciated that by orienting the grasping site 26 of the knotting element to open into or face the loop 21, the segments 49a and 49b can be positioned at the grasping site concomitant with contracture of the loop 21; however, the knotting element can be oriented in many various ways with the grasping site 26 facing into the loop or away from the loop in accordance with procedural use. Although the suture material segments have been described above as being passed through the loop 21 from a first side of the loop to a second side thereof, it should be appreciated that the suture material segments can be passed through the loop from the second side to the first side thereof and that the suture material segments can be passed multiple times through the loop. It should also be appreciated that the knotting element can be positioned at the entry point or at any other location along the tissue being sutured.

Figure 9:
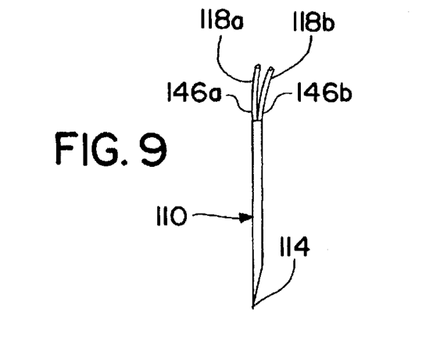
FIG. 9 is a broken side view of a modification of a needle for use in the suturing apparatus according to the present invention.

A modification of a needle for the suturing apparatus according to the present invention is illustrated in FIG. 9 and includes a straight needle 110 having an angled distal tip 114 for penetrating tissue with ends 146a and 146b of suture material length portions 118a and 118b, respectively, secured to a proximal end of needle 110.

Figures 10, 11:
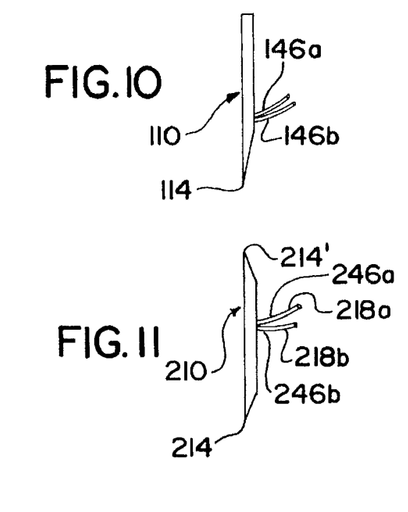
FIG. 10 is a broken side view showing an alternative arrangement for securing the length portions of suture material to the needle of FIG. 9.
FIG. 11 is a broken side view of another modification of a needle for use in the suturing apparatus according to the present invention.
Figure 10A:
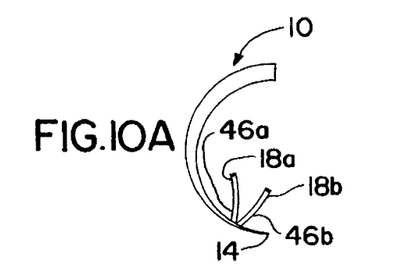
FIG. 10A is a broken side view showing an alternative arrangement for securing the length portions of suture material to the needle of FIG. 1.

FIG. 10 illustrates needle 110 having ends 146a and 146b, respectively, secured thereto at an intermediate position between distal tip 114 and the proximal end of the needle. FIG. 10a illustrates curved needle 10 having ends 46a and 46b of suture material length portions 18a and 18b secured thereto adjacent distal tip 14.

Figure 11A:
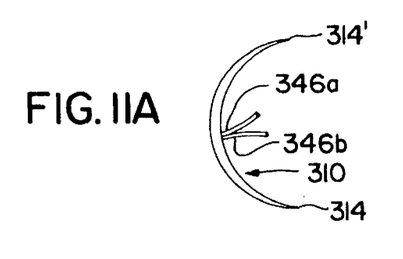
FIG. 11A is a broken side view of still another modification of a needle for use in the suturing apparatus according to the present invention.

FIG. 11 illustrates a straight needle 210 having an angled or beveled distal tip 214 and an angled or beveled proximal tip 214' for penetrating tissue with ends 246a and 246b of suture material length portions 218a and 218b, respectively, attached to the needle 210 mid-way between the distal and proximal tips. FIG. 11a illustrates an arrangement similar to that shown in FIG. 11 except that the needle includes a curved needle 310 having a sharp distal tip 314 and a sharp proximal tip 314' for penetrating tissue. Needles 210 and 310 are particularly advantageous for use in procedures where the distal tip is used to penetrate forwardly through the tissue, and the proximal tip is used to penetrate rearwardly through the tissue as disclosed in the prior application.

Figure 12:
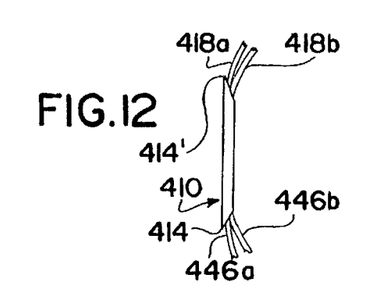
FIG. 12 is a broken side view of a further modification of a needle for use in the suturing apparatus according to the present invention and illustrating another arrangement for securing the length portions of suture material to the needle.
Figure 12A:
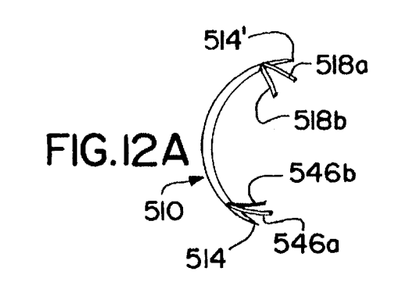
FIG. 12A is a broken side view of yet a further modification of a needle for use in the suturing apparatus according to the present invention.

FIG. 12 illustrates a straight needle 410 that is hollow and has a sharp distal tip 414 and a sharp proximal tip 414' for penetrating tissue with the segments 446a and 446b of suture material length portions 418a and 418b passing entirely through the hollow needle. FIG. 12a illustrates an arrangement similar to that shown in FIG. 12 except that the needle includes a curved needle 510. Various procedures in which hollow needles are particularly useful are disclosed in the prior application.

Figure 13:
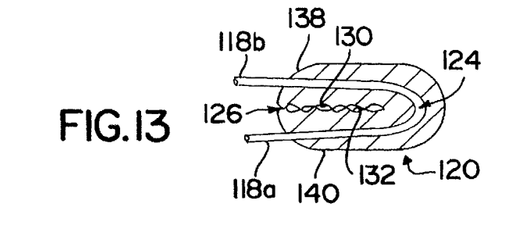
FIG. 13 is a broken side view, partly in section, of a modification of a knotting element for use in the suturing apparatus according to the present invention.
Figure 14:
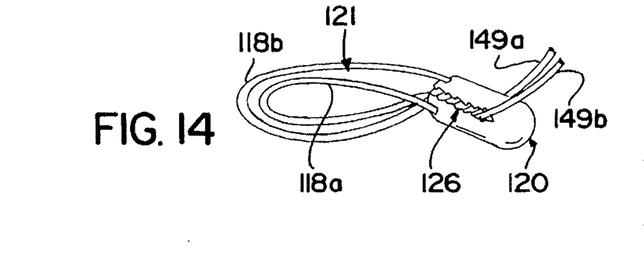
FIG. 14 is a broken perspective view illustrating use of the knotting element of FIG. 13.

FIG. 13 illustrates an alternative knotting element 120, similar to knotting element 20, except that knotting element 120 has an oval configuration in cross-section and is spring biased to be normally disposed in a closed position wherein there is little or no space between opposed surfaces 130 and 132. Knotting element 120 is movable to an open or suture material-receiving portion to receive segments of the first and second length portions with the use of suitable instruments to move jaws 138 and 140 away from one another or by forcibly inserting the segments between the opposed surfaces of the jaws. FIG. 14 illustrates segments 149a and 149b of suture material length portions 118a and 118b passing through the loop 121 between length portions 118a and 118b to be received by the grasping site 126 of knotting element 120. Various spring-loaded or spring biased knotting elements suitable for use in the subject invention are disclosed in the prior application.

Figures 15, 17:
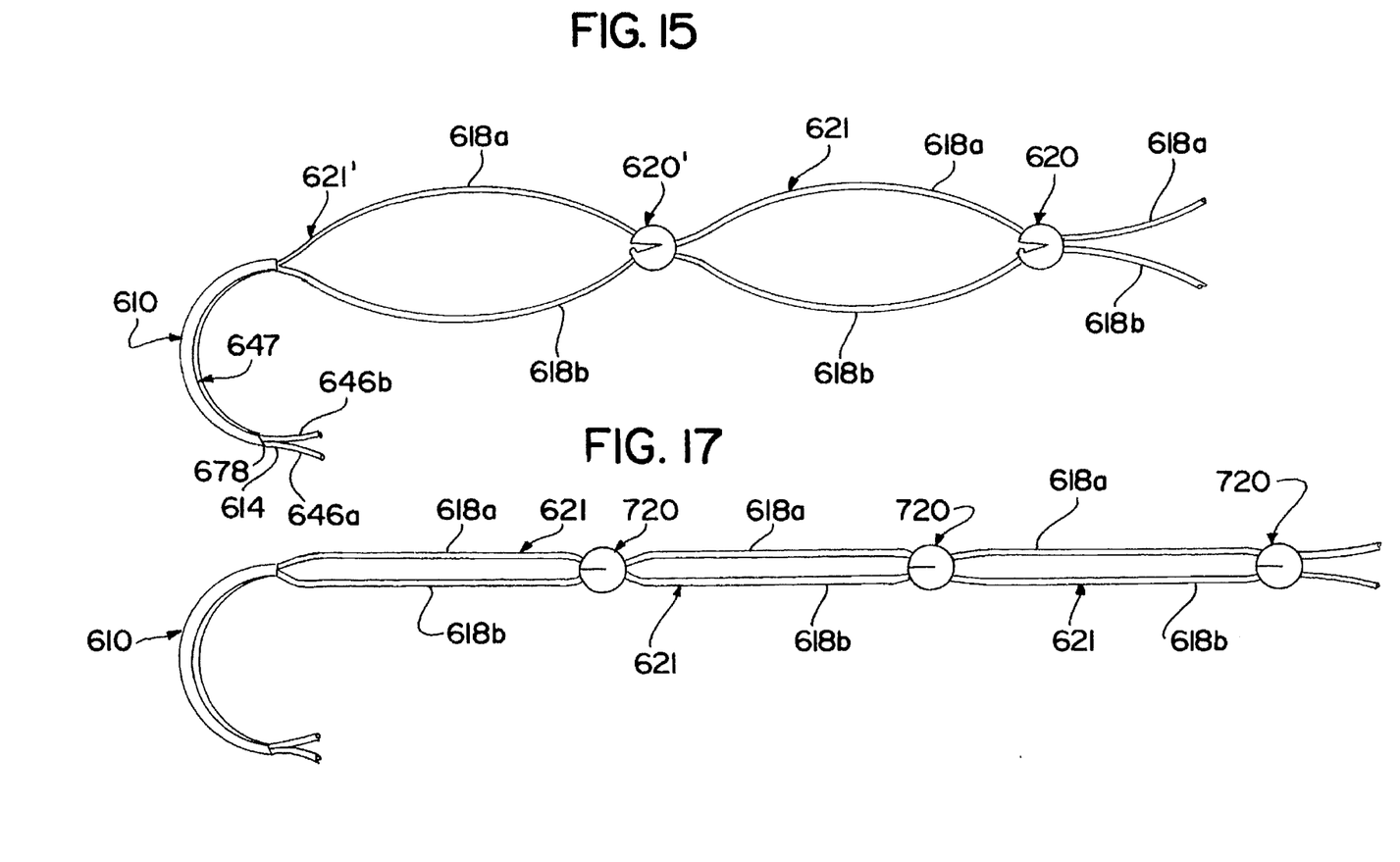
FIG. 15 is a broken side view of a modification of a suturing apparatus according to the present invention.
FIG. 17 is a broken side view of another modification of a suturing apparatus according to the present invention.
Figure 16:
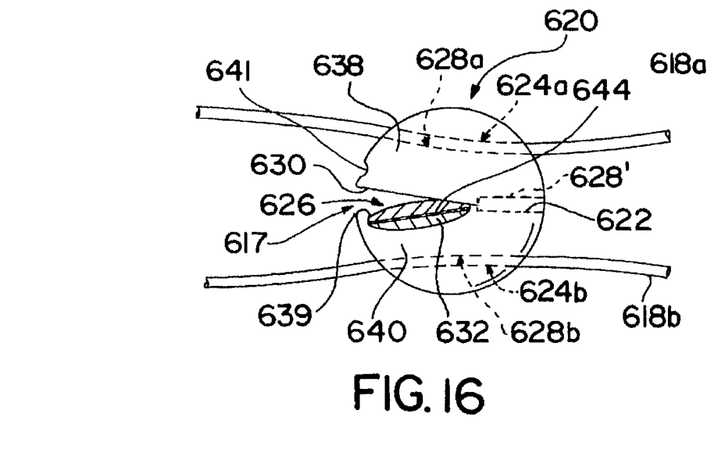
FIG. 16 is a broken side view of the knotting element of the suturing apparatus of FIG. 15.

FIG. 15 illustrates a modification of a suturing apparatus including a suture supply and a needle 610. The suture supply includes two lengths of filamentous suture material 618a and 618b together carrying at least one knotting element 620, a plurality of knotting elements 620 being shown. Knotting element 620 is best shown in FIG. 16 and includes bores 628a and 628b extending lengthwise through jaws 638 and 640, respectively, allowing passage through the knotting element by the lengths of suture material 618a and 618b, respectively. Accordingly, the lengths of suture material 618a and 618b define suture material length portions 618a and 618b between adjacent knotting elements and between the distalmost knotting element 620 and the needle 610. It should be appreciated that length portions 618a and 618b can both pass through the same bore in the knotting element such as a centrally located bore 628' aligned with mouth 617 as shown in dotted lines in FIG. 16. The needle 610 is hollow allowing passage therethrough by the ends 646a and 646b of the lengths of suture material 618a and 618b, respectively, and the ends 646a and 646b can be secured in a notch 678 in the needle 610 as disclosed in the prior application. The needle 610 has a slot 647 extending the entire length thereof allowing movement of knotting elements 620 along the needle as disclosed in the prior application. With the lengths of suture material 618a and 618b coupled to the needle 610, contractible loops 621 are defined between adjacent knotting elements and between the distalmost knotting element 620' and the proximal end of needle 610. The number of loops 621 provided can correspond to the number of stitches expected to be made such that the loops define contractible loop stitch segments or can be essentially indefinite by utilizing a package, such as a spool. The length of the contractible loop stitch segments can vary in accordance with the type of stitch to be performed and can be adjustable by arranging the knotting elements 620 to be slidably carried by the lengths of suture material 618a and 618b as illustrated in FIG. 16 and as disclosed in the prior application. Bores 128a and 128b can follow any desirable straight or non-straight angular or curved path through the knotting elements 620 to form attachment sites 624a and 624b for the lengths of suture material, and the configuration of the paths can be selected to immovable fix the position of the knotting elements where desired.

Knotting elements 620, as best shown in FIG. 16, are similar to knotting element 20 and include a spherical body 622 with a grasping site 626 defined between opposed surfaces 630 and 632 of jaws 638 and 640, respectively. Jaw 640 terminates at a locking protrusion 639, and jaw 638 terminates at a locking lip 641 having a configuration complimentary to the configuration of protrusion 639 whereby the jaws can be locked together as well as being plastically deformed to grasp the suture material. Opposed surfaces 630 and 632 are provided with knurled protrusions, and a groove 644 extends longitudinally along opposed surface 632 for receiving a protruding tongue (not shown) on opposed surface 630 when the jaws 638 and 640 are moved to the closed position as disclosed in the prior application.

Where the suture supply includes a single knotting element 620, the suture supply can be combined with a needle, such as the hollow needle 610, to form a suturing apparatus for use in forming a single suture stitch in the manner previously described for the suturing apparatus of FIG. 1, the needle 610 being separable from the lengths of suture material by manipulating the needle 610 to cause the suture material length portions to pass through the slot 647. Additionally, the suturing apparatus can be used as described in the prior application by driving the distal end 614 of the needle 610 distally through an entry point to pass through one or more tissue portions to exit the tissue at an exit point. Once the ends 646a and 646b have passed through the tissue, the needle is moved proximally causing the double filament of suture material to pass through slot 647 and is withdrawn or backed out proximally from the tissue leaving the suture material in place. Segments of the suture material length portions exiting the tissue are passed through the distalmost loop 621' and are pulled to contract the loop 621' and position the segments in engagement with knotting element 620'. Depending on the orientation of the grasping site, the suture material segments can be positioned to be received by the grasping site concomitant with contracture of the loop. The suture material length portions are pulled to tension the suture stitch, and the knotting element is closed and plastically deformed for additional securement of the thusly formed suture. Any excess suture material is cut, and the needle and any excess suture material are removed from the body.

Where the suture supply includes a plurality of knotting elements as shown in FIG. 15, the suturing apparatus formed by the suture supply and the needle 610 can be used in the manner described in the prior application to form a plurality of suture stitches. For example, the needle 610 is driven forwardly or distally through tissue from an entry point to pull the suture material length portions 618a and 618b through the tissue along with the needle to exit the tissue at an exit point, and the needle can be driven with a suturing instrument as disclosed in the prior application. Once the ends 646a and 646b of the suture material length portions 618a and 618b have exited the tissue, an instrument is utilized to grasp the ends 646a and 646b adjacent the exit point. The ends 646a and 646b are removed from the notch, and the needle is moved proximally or backed out through the tissue along the length portions of the suture material to exit the tissue at the entry point while the suture material length portions are held by the instrument. The needle is moved proximally along the suture material length portions until the distal end of the needle is positioned just proximally of the distalmost knotting element 620'. The instrument is then manipulated to pass the segments of the suture material length portions extending from the exit point through the distalmost loop 621'. The suture material length portions are pulled to contract loop 621', and the suture material segments are positioned to be received by the grasping site to effect a knot for a stitch segment formed between the ends of the suture material length portions and the distalmost knotting element to form a first stitch. The suture material length portions are pulled to tension or tighten the suture stitch to adjustably approximate the tissue, and the knotting element is closed by plastically deforming the jaws to secure the thusly tightened suture stitch. Once tying has been completed by deforming the knotting element to grasp the suture material, the needle 610 is angled relative to the suture material to cause new segments of the suture material length portions adjacent the distal end 614 to enter the notch to be held thereby, and the suture material length portions are cut or severed proximally of the knotting element 620' to separate the thusly formed tightened suture stitch from the suture material held by the needle. Once the stitch has been completed, the suturing apparatus is ready to be used to form a second stitch without requiring removal of the suturing apparatus from the body in that the new segments of suture material secured in the notch define new ends and the next knotting element defines a new distalmost knotting element ready for use to tie the second stitch.

Figure 18:
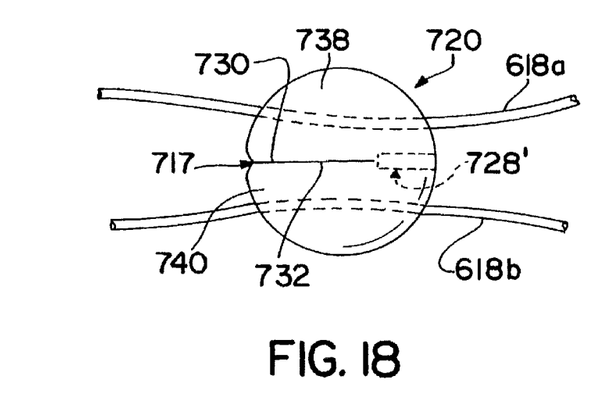
FIG. 18 is a broken side view of the knotting element of the suturing apparatus of FIG. 17.

Another modification of a suture supply is disclosed in FIG. 17 and is similar to that shown in FIG. 15 except that the knotting elements 720 for the suture supply of FIG. 17 are spring-loaded, the suture supply of FIG. 17 being shown coupled with needle 610. Knotting elements 720, as best shown in FIG. 18, have bores 728a and 728b allowing passage therethrough by lengths of suture material 618a and 618b, respectively, and are similar to knotting element 20 except that knotting elements 720 are spring-loaded to be biased to a closed position wherein opposed surfaces 730 and 732 are disposed adjacent or in contact with one another. As disclosed in the prior application, knotting element 720 can be manually moved to an open position with the use of a suitable instrument, such as forceps, to spread or move jaws 738 and 740 away from one another to permit segments of suture material to be received by the grasping site; or, alternatively, the suture material segments can be forcibly inserted or slid between the jaws 738 and 740.

Figure 19:
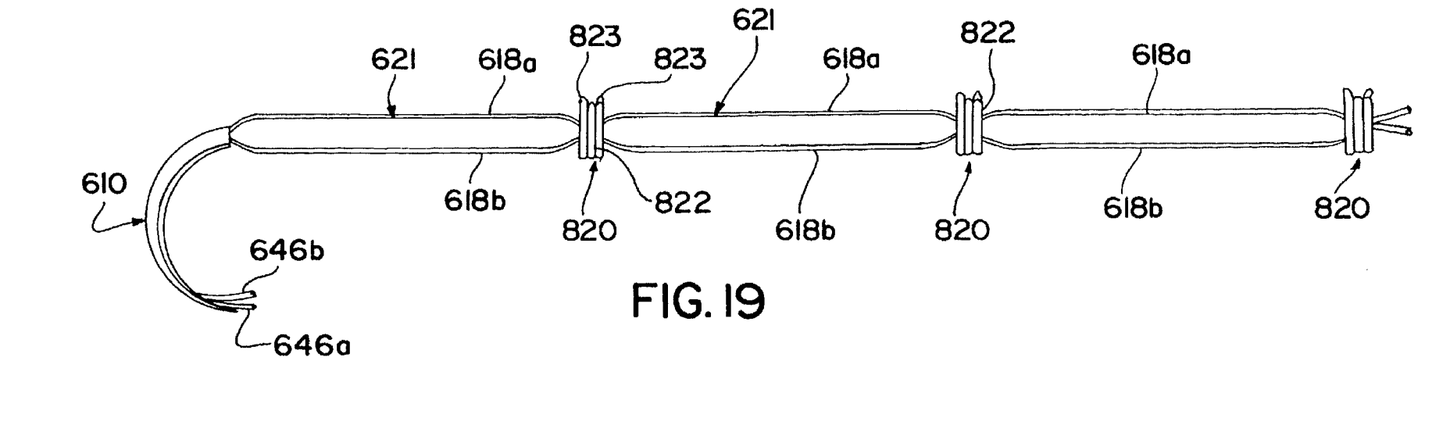
FIG. 19 is a broken side view of a further modification of a suturing apparatus according to the present invention.
Figure 20:
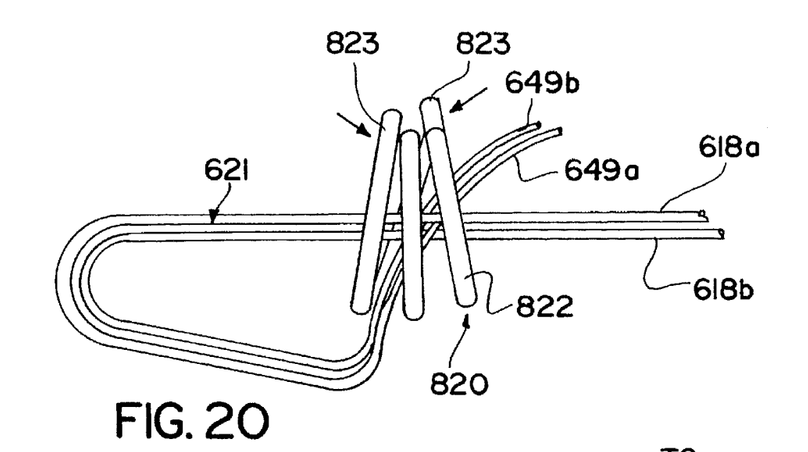
FIG. 20 is a broken side view of the knotting element of the suturing apparatus of FIG. 19.

Another modification of a suturing apparatus including a suture supply and a needle is shown in FIG. 19 wherein the suturing apparatus is similar to that shown in FIG. 15 except that the suturing apparatus of FIG. 19 includes coiled knotting elements 820. Knotting elements 820 are arranged in series along first and second length portions 618a and 618b having ends 646a and 646b passing through needle 610. Knotting elements 820 each include a coiled member or body 822 made up of a plurality of coils or loops having a helical, cylindrical or spiral configuration and made of any suitable absorbable or non-absorbable material. Body 822 is normally disposed in a first position wherein the body is collapsed or closed with the coils or loops thereof adjacent or in contact with one another as shown in FIG. 19. Protrusions 823 extend in the same direction from one side of the outermost coils; and, during use, the protrusions 823 are compressed in the direction of the arrows as shown in FIG. 20 causing the outermost coils or loops to pivot or rotate about an adjacent inner coil to be spread apart at the opposite side of the body in a second position therefor. With the coils or loops spread apart, segments 649a and 649b of length portions 618a and 618b can be passed through loop 621 and through two spaced coils to be received by the grasping site of the knotting element, the two coils defining opposed surfaces for receiving the segments therebetween. Upon removal of the compressive force on knotting element 820, the knotting element will return to the first position with segments 649a and 649b gripped by the opposed surfaces of the two coils. Depending on the materials and/or structure of the knotting element 820, the knotting element can be plastically deformed to further secure the suture stitch.

It should be appreciated that the length portions can be attached or connected to the knotting element 820 in many various ways as disclosed hereinabove and in the prior application such as passing through a central passage of the knotting element as shown in FIG. 20, passing through a bore in one or more of the coils of the knotting element, being wound or wrapped around the coils or being clamped by the coils in the first position, for example. The knotting element 820 can be movable or fixed along the length portions; and, where the length portions pass through a central passage of the knotting element, the central passage can be sized to frictionally retain the length portions. Where the length portions are attached to the knotting element by being clamped between the coils, the position of the knotting element can be adjusted when the knotting element is moved to the second position. When the length portions are positioned between the coils to provide an attachment site or a grasping site, it should be appreciated that the length portions can be positioned between multiple pairs of coils, and that the suture material can be wrapped around the knotting element. In addition to the coil or loop structure shown herein, it should be appreciated that various knotting elements normally disposed in a collapsed position and movable, such as by squeezing, to an open or expanded position can be utilized in the present invention.

Figure 21:
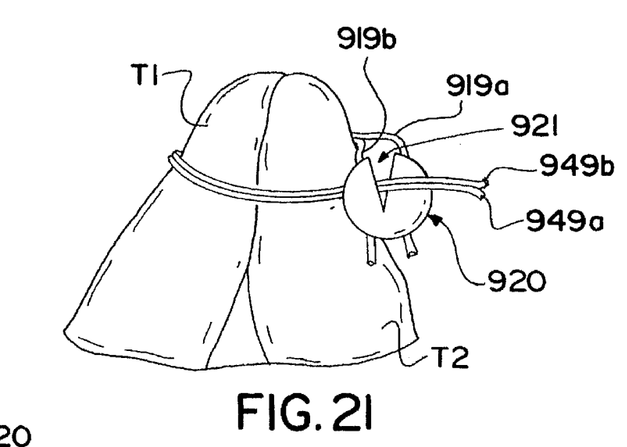
FIG. 21 is a broken perspective view, partly in section, illustrating use of an alternative suture supply according to the present invention.
Figure 22:
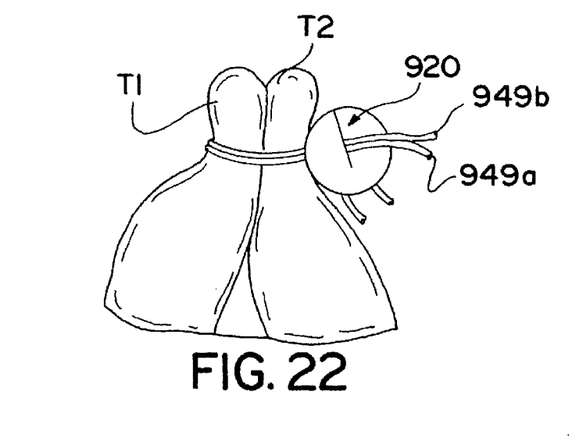
FIG. 22 is a broken perspective view illustrating use of the suture supply of FIG. 21 to form a completed ligature.

FIGS. 21 and 22 illustrate use of an alternative suture supply wherein the length portions 918a and 918b connected by knotting element 920 are positioned to encircle anatomical tissue portions T1 and T2 such that the length portions extend from the knotting element 920 around the tissue portions T1 and T2 and back to the knotting element without passing through the tissue portions. Segments 949a and 949b of the length portions are passed through loop 921 and positioned to be received by the grasping site of the knotting element 920, which is similar to knotting element 20. The length portions are tensioned to adjustably tighten the thusly formed ligature, and the knotting element is plastically deformed to secure the thusly formed tensioned ligature as shown in FIG. 22.

The suture supply of FIG. 20 can include one or more knotting elements and can be used with a needle, which can be moved proximally to position the distal end thereof proximally of the distalmost knotting element to engage new ends or segments of the next length portions for use in forming another ligature or stitch once the length portions have been cut proximally of the distalmost knotting element 620' as described above.

The various suturing apparatus, suture supply, suturing instruments and methods of suturing disclosed in the prior application can include or be utilized with two or more length portions of filamentous suture material as disclosed herein. With the use of multiple length portions to form a contractible loop, segments of the length portions are confined within the loop for enhanced ease of suturing and greater control. When the loop is contracted, the segments will be clamped or gripped therein for enhanced securement. Positioning the suture material to be received by the grasping site of the knotting element is facilitated by confinement of the segments by the loop. Additionally, the knotting elements can be oriented to allow positioning of the suture material at the grasping site concomitant with contracture of the loop.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A suturing apparatus comprising
   a needle having a sharp distal end for penetrating anatomical tissue;
   first and second length portions of filamentous suture material having ends received by said needle; and
   a knotting element connected with first segments of said first and second length portions to form a loop with said suture material extending from said needle to said knotting element and back to said needle, said loop being contractible to confine therein second segments of said first and second length portions after said needle has penetrated the anatomical tissue and said second segments have been passed through said loop, said knotting element having a grasping site including a pair of opposed surfaces for grasping said second segments therebetween, said knotting element having a first position for receiving said second segments between said opposed surfaces, said opposed surfaces in said first position being spaced from one another to define a mouth therebetween, said mouth facing into said loop to receive said second segments passed through said ligature loop, said knotting element having a second position for non-releasably grasping said second segments between said opposed surfaces to effect a knot after said needle has been passed through said loop and said suture material has been tensioned and received between said opposed surfaces.

2. A suturing apparatus as recited in claim 1 wherein said ends of said first and second length portions are secured to said needle adjacent said distal end.

3. A suturing apparatus as recited in claim 1 wherein said needle has a proximal end and said ends of said first and second length portions are secured to said proximal end of said needle.

4. A suturing apparatus as recited in claim 1 wherein said needle has a proximal end and said ends of said first and second length portions are secured to said needle at a position between said distal end and said proximal end of said needle.

5. A suturing apparatus as recited in claim 1 wherein said needle has a proximal end longitudinally spaced from said distal end and a lumen passing longitudinally therethrough and said first and second length portions pass through said lumen.

6. A suturing apparatus as recited in claim 5 wherein said needle has a longitudinal slot extending between said proximal and distal ends whereby said knotting element can move externally along said needle.

7. A suturing apparatus as recited in claim 1 wherein said knotting element includes a pair of jaws defining said opposed surfaces and being biased to normally position said opposed surfaces in contact with each other.

8. A suturing apparatus as recited in claim 1 wherein said suture material is stretchable.

9. A suturing apparatus as recited in claim 1 wherein said knotting element includes a pair of Jaws defining said opposed surfaces, said jaws being normally in said first position and being plastically deformable to said second position.

10. A suturing apparatus as recited in claim 1 wherein said knotting element includes locking structure for locking said knotting element in said second position.

11. A suturing apparatus as recited in claim 1 wherein said first and second length portions are formed of a single length of suture material extending from said needle and through said knotting element back to said needle.

12. A suturing apparatus as recited in claim 1 wherein said first and second length portions are formed by separate lengths of suture material extending from said needle and terminating at said knotting element.

13. A suture supply comprising first and second lengths of filamentous suture material;

a plurality of knotting elements arranged in series along said first and second lengths and each connected between said first length and said second length to form a plurality of contractible loops with said suture material, each of said knotting elements having a grasping site for grasping a segment of said first length and a segment of said second length to act as a knot for stitch segments defined between adjacent knotting elements, each of said grasping sites including an opening comprised of opposed surfaces spaced from one another defining a mouth therebetween, said mouth facing into one of said loops for receiving said segments when said first and second lengths are passed through said one loop, said knotting elements having a first position wherein said mouths are open to receive said segments and a second position wherein said mouths are closed to non-releasably grasp said segments.

14. A suture supply as recited in claim 13 wherein said knotting elements are immovably secured to said first and second lengths at spaced locations therealong.

15. A suture supply as recited in claim 13 wherein each of said knotting elements includes opposed jaws spring biased to contact each other.

16. A suture supply as recited in claim 13 wherein said knotting elements are slidably carried on said first and second lengths.

17. A suture supply as recited in claim 13 wherein said first and second lengths pass entirely through at least some of said knotting elements.

18. A suture supply comprising a first length portion and a second length portion of filamentous suture material, said first and second length portions having end portions connected to one another; and a knotting element connected between said first and second length portions proximally of said end portions to form a contractible loop defined by said first and second length portions and said knotting element, said knotting element having at least one attachment site at which segments of said first and second length portions are secured to said knotting element and at least one grasping site for grasping other segments of said first and second length portions to tie a stitch formed when said other segments are passed through said loop and said first and second length portions are tensioned to contract said loop, said knotting element including a member having a plurality of coils, said member being movable from a first position wherein said coils are disposed close to one another to a second position wherein said coils are disposed further away from one another to receive said other segments between said coils, said member being movable from said second position back to said first position to non-releasably grip said other segments between said coils.

19. A method of suturing tissue comprising the steps of providing first and second length portions of filamentous suture material carrying a knotting element connecting first segments of the first and second length portions with one another and a needle coupled with the first and second length portions to form a contractible loop with the suture material extending from the needle to the knotting element and back to the needle;

penetrating the tissue with the needle from an entry point to an exit point to pass the first and second length portions through the tissue;

passing second segments of the first and second length portions exiting the tissue at the exit point through the loop to form a stitch segment extending from the knotting element through the tissue and back to the knotting element;

positioning the second segments in an opening of the knotting element, said opening comprised of opposed surfaces spaced from one another defining a mouth therebetween, with the mouth in an open position;

tightening the stitch segment to a desired tension with the second segments positioned in the mouth of the knotting element with the mouth in the open position; and plastically deforming the knotting element to move the mouth to a closed position to grasp the second segments with the knotting element and form a knot for the tightened stitch segment.

20. A method of forming a stitch in anatomical tissue comprising the steps of providing a first length portion and a second length portion of filamentous suture material carrying a knotting element connecting a first segment of the first length portion with a first segment of the second length portion to form a contractible loop defined by the first and second length portions and the knotting element;

positioning the first and second length portions around tissue without passing the first and second length portions through the tissue;

passing a second segment of the first length portion and a second segment of the second length portion through the loop to form a stitch extending from the knotting element around the tissue and back to the knotting element;

positioning the second segments in an opening of the knotting element, said opening comprised of opposed surfaces spaced from one another defining a mouth therebetween, with the mouth in an open position;

tightening the stitch to a desired tension with the second segments positioned in the mouth of the knotting element with the mouth in the open position; and closing the mouth of the knotting element to non-releasably grasp the second segments to secure the stitch.

* * * * *